United States Patent [19]
Schneider et al.

[11] Patent Number: 6,110,443
[45] Date of Patent: *Aug. 29, 2000

[54] DRY STABLE FORMATION TO PRODUCE MICROBUBBLE SUSPENSION FOR ULTRASOUND

[75] Inventors: Michel Schneider, Troinex, Switzerland; Daniel Bichon, Montpellier, France; Philippe Bussat, Collonges S/Saleve, France; Jerome Puginier, Le Chable-Beaunont, France; Eva Hybl-Sutherland, Geneva, Switzerland

[73] Assignee: Bracco International N.V., Netherlands

[ * ] Notice: This patent is subject to a terminal disclaimer.

[21] Appl. No.: 08/853,936

[22] Filed: May 9, 1997

Related U.S. Application Data

[62] Division of application No. 08/456,385, Jun. 1, 1995, Pat. No. 5,658,551, which is a division of application No. 08/315,347, Sep. 30, 1994, Pat. No. 5,531,980, which is a division of application No. 08/128,540, filed as application No. PCT/EP91/00620, Apr. 2, 1991, Pat. No. 5,380,519, and a division of application No. 07/775,989, Nov. 20, 1991, Pat. No. 5,271,928.

[30] Foreign Application Priority Data

Apr. 2, 1990 [EP] European Pat. Off. .......... 9081029262

[51] Int. Cl.⁷ ........................................ A61B 8/13

[52] U.S. Cl. ................... 424/9.51; 424/9.52; 424/450

[58] Field of Search ................ 424/9.52, 9.51, 424/450; 600/431

[56] References Cited

U.S. PATENT DOCUMENTS

| | | |
|---|---|---|
| 4,192,859 | 3/1980 | Mackaness . |
| 4,224,179 | 9/1980 | Schneider ................................. 264/4.6 |
| 4,229,360 | 10/1980 | Schneider et al. ...................... 264/4.6 |
| 4,370,349 | 1/1983 | Evans et al. . |
| 4,442,843 | 4/1984 | Rasor et al. ............................ 424/9.52 |
| 4,466,442 | 8/1984 | Hilmann et al. . |
| 4,544,545 | 10/1985 | Ryan et al. ............................. 424/1.1 |
| 4,832,941 | 5/1989 | Berwing et al. ............................ 424/9 |
| 4,844,882 | 7/1989 | Widder et al. ......................... 424/9.52 |
| 4,859,363 | 8/1989 | Davis et al. ............................... 516/76 |
| 4,900,540 | 2/1990 | Ryan et al. . |
| 4,927,623 | 5/1990 | Long, Jr. ..................................... 424/5 |
| 5,088,499 | 2/1992 | Unger . |
| 5,089,181 | 2/1992 | Hauser . |
| 5,123,414 | 6/1992 | Unger ..................................... 600/431 |
| 5,271,928 | 12/1993 | Schneider et al. ..................... 424/9.52 |
| 5,283,067 | 2/1994 | Geller et al. . |
| 5,352,436 | 10/1994 | Wheatley et al. ...................... 424/9.52 |
| 5,380,519 | 1/1995 | Schneider et al. ..................... 424/9.51 |
| 5,409,688 | 4/1995 | Quay ..................................... 424/9.52 |
| 5,425,366 | 6/1995 | Reinhardt et al. ................. 128/662.02 |
| 5,531,980 | 7/1996 | Schneider et al. ..................... 424/9.52 |
| 5,536,489 | 7/1996 | Lohrmann et al. .................... 424/9.52 |
| 5,536,490 | 7/1996 | Klaveness et al. .................... 424/9.52 |
| 5,556,610 | 9/1996 | Yan et al. ............................... 424/9.52 |
| 5,567,414 | 10/1996 | Schneider et al. ..................... 424/9.52 |
| 5,643,553 | 7/1997 | Schneider et al. ..................... 424/9.52 |
| 5,658,551 | 8/1997 | Schneider et al. ..................... 424/9.51 |
| 5,711,933 | 1/1998 | Bichon et al. ......................... 424/9.52 |

FOREIGN PATENT DOCUMENTS

| | | |
|---|---|---|
| 052575 | 5/1982 | European Pat. Off. . |
| 0 077 752 | 4/1983 | European Pat. Off. . |
| 0077752 | 4/1983 | European Pat. Off. . |
| 0123235 | 10/1984 | European Pat. Off. . |
| 0131540 | 1/1985 | European Pat. Off. . |
| 0 245 019 | 11/1987 | European Pat. Off. . |
| 0320433 | 6/1989 | European Pat. Off. . |
| 0 324 938 | 7/1989 | European Pat. Off. . |
| 0324938 | 7/1989 | European Pat. Off. . |
| 0 467 031 A2 | 1/1992 | European Pat. Off. . |
| 0327490 | 8/1989 | Germany . |
| 2134869 | 8/1984 | United Kingdom . |
| 2135647 | 9/1984 | United Kingdom . |
| WO 80/02365 | 11/1980 | WIPO . |
| 88/07365 | 10/1988 | WIPO . |
| 88/09165 | 12/1988 | WIPO . |
| WO 89/06978 | 8/1989 | WIPO . |
| WO 89/10118 | 11/1989 | WIPO . |
| WO 92/17212 | 10/1992 | WIPO . |
| WO 92/17213 | 10/1992 | WIPO . |
| WO 92/21382 | 12/1992 | WIPO . |
| WO 92/22247 | 12/1992 | WIPO . |
| WO 93/06869 | 4/1993 | WIPO . |
| WO 93/17718 | 9/1993 | WIPO . |

OTHER PUBLICATIONS deJong et al Ultrasonics 1992 vol. 30 No. 2 pp 95–103 Absorption and scatter of encapsulated gas etc.
deJong et al Ultrasonics 1991 vol. 29 Jul. pp 324–330 Principles and recent developments in ultrasound etc.
Bleeker et al 1990 J. Ultrasound Med 9:461–471, 1990 pp 462–471 On the Application of Ultrsonic Contrast etc.
Feinstein et al JACC vol. 16, No. 2 8/90:316–24 Safety and Efficacy of a New Transpulmonary Ultrasound etc.
Amer Hearts Assn Monograph Circulation Part II vol. 72 No. 4 Oct. 1985 Abstracts of the 58th Scientific Sessions.
Bleeker et al J. Acoust. Soc. Am. 87 (4) Apr. 1990 pp 1792–1797 Ultrasonic characterization of Albunex® etc.
Epstein et al J. Chem. Physics vol. 18, No. 11, Nov. 1950 On the Stability of Gas Bubbles in Liquid–Gas Solutions.
Meltzer et al. Ultrasound in Med & Biol vol. 7 pp 377–384 1981 Transmission of Ultrasonic Contrast etc.
Violante et al Investigative Radiology vol. 26 Nov. Supp 1991 Particle–Stabilized Bubbles for Enhanced etc.
Ohta et al Jpn J Med Ultrasonics vol. 18 No. 4 (1991) Effect of the Contrast Agent and the Agitation Method etc.

(List continued on next page.)

*Primary Examiner*—Gary E. Hollinden
*Attorney, Agent, or Firm*—Nixon & Vanderhye

[57] ABSTRACT

Gas or air filled microbubble suspensions in aqueous phases usable as imaging contrast agents in ultrasonic echography. They contain laminarized surfactants and, optionally, hydrophilic stabilizers. The laminarized surfactants can be in the form of liposomes. The suspensions are obtained by exposing the laminarized surfactants to air or a gas before or after admixing with an aqueous phase.

50 Claims, No Drawings

OTHER PUBLICATIONS

Feinstein et al Am J of Physiologic Imaging 1:12–18 (1986) Myocardial Contrast Echocardiography etc.

Widder et al AJR:147, Aug. 1986 Microbubbles as a Contrast Agent for Neurosonography and Ultrasound– etc.

Schlief Current Opinion in Radiology 1991, 3:198–207 Ultrasound Contrast Agents.

Fobbe et al Furtschr Rontgenstr 154.3 (1991)242–245 Farbkodierte Duplexsonographic und Ultra– etc.

Ophir et al Ultrasound in Med & Biol vol. 15 No. 4 pp 319–333 1989 Contrast Agents in Diagnostic Ultrasound.

Chemical Abstracts, vol. 102, No. 3, Jan. 21, 1985. Maynard et al "Ultrasonic absorption by liposomes", see p. 291, #20001d.

DRY STABLE FORMATION TO PRODUCE MICROBUBBLE SUSPENSION FOR ULTRASOUND

This is a Rule 60 Division of application Ser. No. 08/456,385 U.S. Pat. No. 5,658,551 filed 1 June 1995 which is a division of Ser. No. 08/315,347 filed Sep. 30, 1994 U.S. Pat. No. 5,531,980 which is a division of Ser. No. 08/128,540 filed Sep. 29, 1993 now U.S. Pat. No. 5,380,519 which is a 371 of PCT/EP91/00620 filed Apr. 2, 1991 and is a division of Ser. No. 07/775,989, filed Nov. 20, 1991, now U.S. Pat. No. 5,271,928.

The present invention concerns media adapted for injection into living bodies, e.g. for the purpose of ultrasonic echography and, more particularly, injectable liquid compositions comprising microbubbles of air or physiologically acceptable gases as stable dispersions or suspensions in an aqueous liquid carrier. These compositions are mostly usable as contrast agents in ultrasonic echography to image the inside of blood-stream vessels and other cavities of living beings, e.g. human patients and animals. Other uses however are also contemplated as disclosed hereafter.

The invention also comprises dry compositions which, upon admixing with an aqueous carrier liquid, will generate the foregoing sterile suspension of microbubbles thereafter usable as contrast agent for ultrasonic echography and other purposes.

It is well known that microbodies like microspheres or microglobules of air or a gas, e.g. microbubbles or microballoons, suspended in a liquid are exceptionally efficient ultrasound reflectors for echography. In this disclosure the term of "microbubble" specifically designates air or gas globules in suspension in a liquid which generally results from the introduction therein of air or a gas in divided form, the liquid preferably also containing surfactants or tensides to control the surface properties thereof and the stability of the bubbles. More specifically, one may consider that the internal volume of the microbubbles is limited by the gas/liquid interface, or in other words, the microbubbles are only bounded by a rather evanescent envelope involving the molecules of the liquid and surfactant loosely bound at the gas to liquid junction boundary.

In contrast, the term of "microcapsule" or "microballoon" designates preferably air or gas bodies with a material boundary or envelope formed of molecules other than that of the liquid of suspension, e.g. a polymer membrane wall. Both microbubbles and microballoons are useful as ultrasonic contrast agents. For instance injecting into the blood-stream of living bodies suspensions of gas microbubbles or microballoons (in the range of 0.5 to 10 $\mu$m) in a carrier liquid will strongly reinforce ultrasonic echography imaging, thus aiding in the visualization of internal organs. Imaging of vessels and internal organs can strongly help in medical diagnosis, for instance for the detection of cardiovascular and other diseases.

The formation of suspensions of microbubbles in an injectable liquid carrier suitable for echography can follow various routes. For instance in DE-A- 3529195 (Max-Planck Gesell.), there is disclosed a technique for generating 0.5–50 $\mu$m bubbles in which an aqueous emulsified mixture containing a water soluble polymer, an oil and mineral salts is forced back and forth, together with a small amount of air, from one syringe into another through a small opening. Here, mechanical forces are responsible for the formation of bubbles in the liquid.

M. W. Keller et al. (J. Ultrasound Med. 5 (1986), 439-8) have reported subjecting to ultrasonic cavitation under atmospheric pressure solutions containing high concentrations of solutes such as dextrose, Renografin-76, Iopamidol (an X-ray contrast agent), and the like. There the air is driven into the solution by the energy of cavitation.

Other techniques rely on the shaking of a carrier liquid in which air containing microparticles have been incorporated, said carrier liquid usually containing, as stabilizers, viscosity enhancing agents, e.g. water soluble polypeptides or carbohydrates and/or surfactants. It is effectively admitted that the stability of the microbubbles against decay or escape to the atmosphere is controlled by the viscosity and surface properties of the carrier liquid. The air or gas In the microparticles can consist of inter-particle or intra-crystalline entrapped gas, as well as surface adsorbed gas, or gas produced by reactions with the carrier liquid, usually aqueous. All this is fully described for instance in EP-A- 52.575 (Ultra Med. Inc.) In which there are used aggregates of 1–50 $\mu$m particles of carbohydrates (e.g. galactose, maltose, sorbitol, gluconic acid, sucrose, glucose and the like) in aqueous solutions of glycols or polyglycols, or other water soluble polymers.

Also, in EP-A- 123.235 and 122.624 (Schering, see also EP-A- 320.433) use is made of air trapped in solids. For instance, 122.624 claims a liquid carrier contrast composition for ultrasonic echography containing microparticles of a solid surfactant, the latter being optionally combined with microparticles of a non-surfactant. As explained in this document, the formation of air bubbles in the solution results from the release of the air adsorbed on the surface of the particles, or trapped within the particle lattice, or caught between individual particles, this being so when the particles are agitated with the liquid carrier.

EP-A- 131.540 (Schering) also discloses the preparation of microbubbles suspensions in which a stabilized injectable carrier liquid, e.g. a physiological aqueous solution of salt, or a solution of a sugar like maltose, dextrose, lactose or galactose, without viscosity enhancer, is mixed with microparticles (in the 0.1 to 1 $\mu$m range) of the same sugars containing entrapped air. In order that the suspension of bubbles can develop within the liquid carrier, the foregoing documents recommend that both liquid and solid components be violently agitated together under sterile conditions; the agitation of both components together is performed for a few seconds and, once made, the suspension must then be used immediately, i.e. it should be injected within 5–10 minutes for echographic measurements; this indicates that the bubbles in the suspensions are not longlived and one practical problem with the use of microbubbles suspensions for injection is lack of stability with time. The present invention fully remedies this drawback.

In U.S. Pat. No. 4,466,442 (Schering), there is disclosed a series of different techniques for producing suspensions of gas microbubbles in a liquid carrier using (a) a solution of a tenside (surfactant) in a carrier liquid (aqueous) and (b) a solution of a viscosity enhancer as stabilizer. For generating the bubbles, the techniques used there include forcing at high velocity a mixture of (a), (b) and air through a small aperture; or injecting (a) into (b) shortly before use together with a physiologically acceptable gas; or adding an acid to (a) and a carbonate to (b), both components being mixed together just before use and the acid reacting with the carbonate to generate $CO_2$ bubbles; or adding an overpressurized gas to a mixture of (a) and (b) under storage, said gas being released into microbubbles at the time when the mixture is used for injection.

The tensides used in component (a) of U.S. Pat. No. 4,466,442 comprise lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers. The viscosity raising and stabilizing compounds include for instance mono- and polysaccharides (glucose, lactose, sucrose, dextran, sorbitol); polyols, e.g. glycerol, polyglycols; and polypeptides like proteins, gelatin, oxypolygelatin, plasma protein and the like.

In a typical preferred example of this document, equivalent volumes of (a) a 0.5% by weight aqueous solution of Pluronic® F-68 (a polyoxypropylene-polyoxyethylene polymer) and (b) a 10% lactose solution are vigorously shaken together under sterile conditions (closed vials) to provide a suspension of microbubbles ready for use as an ultrasonic contrast agent and lasting for at least 2 minutes. About 50% of the bubbles had a size below 50 μm.

Although the achievements of the prior art have merit, they suffer from several drawbacks which strongly limit their practical use by doctors and hospitals, namely their relatively short life-span (which makes test reproducibility difficult), relative low initial bubble concentration (the number of bubbles rarely exceeds $10^4$–$10^5$ bubbles/ml and the count decreases rapidly with time) and poor reproducibility of the initial bubble count from test to test (which also makes comparisons difficult). Also it is admitted that for efficiently imaging certain organs, e.g. the left heart, bubbles smaller than 50 μm, preferably in the range of 0.5–10 μm, are required: with longer bubbles, there are risks of clots and consecutive emboly.

Furthermore, the compulsory presence of solid microparticles or high concentrations of electrolytes and other relatively inert solutes in the carrier liquid may be undesirable physiologically In some cases. Finally, the suspensions are totally unstable under storage and cannot be marketed as such; hence great skill is required to prepare the microbubbles at the right moment just before use.

Of course there exists stable suspensions of microcapsules, i.e. microballoons with a solid, air-sealed rigid polymeric membrane which perfectly resist for long storage periods in suspension, which have been developed to remedy this shortcoming (see for instance K. J. Widder, EP-A- 324.938); however the properties of microcapsules in which a gas is entrapped inside solid membrane vesicles essentially differ from that of the gas microbubbles of the present invention and belong to a different kind of art; for instance while the gas microbubbles discussed here will simply escape or dissolve in the blood-stream when the stabilizers in the carrier liquid are excreted or metabolized, the solid polymer material forming the walls of the aforementioned micro-balloons must eventually be disposed of by the organism being tested which may impose a serious afterburden upon it. Also capsules with solid, non-elastic membrane may break irreversibly under variations of pressure.

The composition of the present invention, as defined in claim 1, fully remedies the aforementioned pitfalls.

The term "lamellar form" defining the condition of at least a portion of the surfactant or surfactants of the present composition indicates that the surfactants, in strong contrast with the microparticles of the prior art (for instance EP-A-123.235), are in the form of thin films involving one or more molecular layers (in laminate form). Converting film forming surfactants into lamellar form can easily be done for instance by high pressure homogenization or by sonication under acoustical or ultrasonic frequencies. In this connection, it should be pointed out that the existence of liposomes is a well known and useful illustration of cases in which surfactants, more particularly lipids, are in lamellar form.

Liposome solutions are aqueous suspensions of microscopic vesicles, generally spherically shaped, which hold substances encapsulated therein. These vesicles are usually formed of one or more concentrically arranged molecular layers (lamellae) of amphipatic compounds, i.e. compounds having a lipophobic hydrophilic moiety and a lipophilic hydrophobic moiety. See for instance "Liposome Methodology", Ed. L. D. Leserman et al, Inserm 136, 2–8 May 1982). Many surfactants or tensides, including lipids, particularly phospholipids, can be laminarized to correspond to this kind of structure. In this invention, one preferably uses the lipids commonly used for making liposomes, for instance the lecithins and other tensides disclosed in more detail hereafter, but this does in no way preclude the use of other surfactants provided they can be formed into layers or films.

It is important to note that no confusion should be made between the present invention and the disclosure of Ryan (U.S. Pat. No. 4,900,540) reporting the use of air or gas filled liposomes for echography. In this method Ryan encapsulates air or a gas within liposomic vesicles; in embodiments of the present invention microbubbles or air or a gas are formed in a suspension of liposomes (i.e. liquid filled liposomes) and the liposomes apparently stabilize the microbubbles. In Ryan, the air is inside the liposomes, which means that within the bounds of the presently used terminology, the air filled liposomes of Ryan belong to the class of microballoons and not to that of the microbubbles of the present invention.

Practically, to achieve the suspensions of microbubbles according to the invention, one may start with liposomes suspensions or solutions prepared by any technique reported in the prior art, with the obvious difference that in the present case the liposomic vesicles are preferably "unloaded", i.e. they do not need to keep encapsulated therein any foreign material other than the liquid of suspension as is normally the object of classic liposomes. Hence, preferably, the liposomes of the present invention will contain an aqueous phase identical or similar to the aqueous phase of the solution itself. Then air or a gas is introduced into the liposome solution so that a suspension of microbubbles will form, said suspension being stabilized by the presence of the surfactants in lamellar form. Notwithstanding, the material making the liposome walls can be modified within the scope of the present invention, for instance by covalently grafting thereon foreign molecules designed for specific purposes as will be explained later.

The preparation of liposome solutions has been abundantly discussed in many publications, e.g. U.S. Pat. No. 4,224,179 and WO-A-88/09165 and all citations mentioned therein. This prior art is used here as reference for exemplifying the various methods suitable for converting film forming tensides into lamellar form. Another basic reference by M. C. Woodle and D. Papahadjopoulos is found in "Methods in Enzymology" 171 (1989), 193.

For instance, in a method disclosed in D. A. Tyrrell et al, Biochimica & Biophysica Acta 457 (1976), 259–302, a mixture of a lipid and an aqueous liquid carrier is subjected to violent agitation and thereafter sonicated at acoustic or ultrasonic frequencies at room or elevated temperature. In the present invention, it has been found that sonication without agitation is convenient. Also, an apparatus for making liposomes, a high pressure homogenizer such as the Microfluidizer®, which can be purchased from Microfluidics Corp., Newton, Mass. 02164 USA, can be used advantageously. Large volumes of liposome solutions can be prepared with this apparatus under pressures which can reach 600–1200 bar.

In another method, according to the teaching of GB-A-2,134,869 (Squibb), microparticles (10 µm or less) of a hydrosoluble carrier solid (NaCl, sucrose, lactose and other carbohydrates) are coated with an amphipatic agent; the dissolution of the coated carrier in an aqueous phase will yield liposomic vesicles. In GB-A- 2,135,647 insoluble particles, e.g. glass or resin microbeads are coated by moistening in a solution of a lipid in an organic solvent followed by removal of the solvent by evaporation. The lipid coated microbeads are thereafter contacted with an aqueous carrier phase, whereby liposomic vesicles will form in that carrier phase.

The introduction of air or gas into a liposome solution in order to form therein a suspension of microbubbles can be effected by usual means, inter alia by injection, that is, forcing said air or gas through tiny orifices into the liposome solution, or simply dissolving the gas in the solution by applying pressure and thereafter suddenly releasing the pressure. Another way is to agitate or sonicate the liposome solution in the presence of air or an entrappable gas. Also one can generate the formation of a gas within the solution of liposomes itself, for instance by a gas releasing chemical reaction, e.g. decomposing a dissolved carbonate or bicarbonate by acid. The same effect can be obtained by dissolving under pressure a low boiling liquid, for instance butane, in the aqueous phase and thereafter allowing said liquid to boll by suddenly releasing the pressure.

Notwithstanding, an advantageous method is to contact the dry surfactant in lamellar or thin film form with air or an adsorbable or entrappable gas before introducing said surfactant into the liquid carrier phase. In this regard, the method can be derived from the technique disclosed in GB-A-2,135,647, i.e. solid microparticles or beads are dipped in a solution of a film forming surfactant (or mixture of surfactants) in a volatile solvent, after which the solvent is evaporated and the beads are left in contact with air (or an adsorbable gas) for a time sufficient for that air to become superficially bound to the surfactant layer. Thereafter, the beads coated with air filled surfactant are put into a carrier liquid, usually water with or without additives, whereby air bubbles will develop within the liquid by gentle mixing, violent agitation being entirely unnecessary. Then the solid beads can be separated, for instance by filtration, from the microbubble suspension which is remarkably stable with time.

Needless to say that, instead of insoluble beads or spheres, one may use as supporting particles water soluble materials like that disclosed in GB-A- 2,134,869 (carbohydrates or hydrophilic polymers), whereby said supporting particles will eventually dissolve and final separation of a solid becomes unnecessary. Furthermore in this case, the material of the particles can be selected to eventually act as stabilizer or viscosity enhancer wherever desired.

In a variant of the method, one may also start with dehydrated liposomes, i.e. liposomes which have been prepared normally by means of conventional techniques in the form of aqueous solutions and thereafter dehydrated by usual means, e.g. such as disclosed in U.S. Pat. No. 4,229,360 also incorporated herein as reference. One of the methods for dehydrating liposomes recommended in this reference is freeze-drying (lyophilization), i.e. the liposome solution is frozen and dried by evaporation (sublimation) under reduced pressure. Prior to effecting freeze-drying, a hydrophilic stabilizer compound is dissolved in the solution, for instance a carbohydrate like lactose or sucrose or a hydrophilic polymer like dextran, starch, PVP, PVA and the like. This is useful in the present invention since such hydrophilic compounds also aid in homogenizing the microbubbles size distribution and enhance stability under storage. Actually making very dilute aqueous solutions (0.1–10% by weight) of freeze-dried liposomes stabilized with, for instance, a 5:1 to 10:1 weight ratio of lactose to lipid enables to produce aqueous microbubbles suspensions counting $10^8$–$10^9$ microbubbles/ml (size distribution mainly 0.5–10 µm) which are stable for at least a month (and probably much longer) without significant observable change. And this is obtained by simple dissolution of the air-stored dried liposomes without shaking or any violent agitation. Furthermore, the freeze-drying technique under reduced pressure is very useful because it permits, after drying, to restore the pressure above the dried liposomes with any entrappable gas, i.e. nitrogen, $CO_2$, argon, methane, FREON, etc., whereby after dissolution of the liposomes processed under such conditions suspensions of microbubbles containing the above gases are obtained.

Microbubbles suspensions formed by applying gas pressure on a dilute solution of laminated lipids in water (0.1–10% by weight) and thereafter suddenly releasing the pressure have an even higher bubble concentration, e.g. in the order of $10^{10}$– $10^{11}$ bubbles/ml. However, the average bubble size is somewhat above 10 µm, e.g. in the 10–50 µm range. In this case, bubble size distribution can be narrowed by centrifugation and layer decantation.

The tensides or surfactants which are convenient in this invention can be selected from all amphipatic compounds capable of forming stable films in the presence of water and gases. The preferred surfactants which can be laminarized include the lecithins (phosphatidyl-choline) and other phospholipids, inter alia phosphatidic acid (PA), phosphatidyl-inositol phosphatidyl-ethanolamine (PE), phosphatidyl-serine (PS), phosphatidyl-glycerol (PG), cardiolipin (CL), sphingomyelins, the plasmogens, the cerebrosides, etc. Examples of suitable lipids are the phospholipids in general, for example, natural lecithins, such as egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline, with egg lecithin or soya bean lecithin being preferred. Additives like cholesterol and other substances (see below) can be added to one or more of the foregoing lipids in proportions ranging from zero to 50% by weight.

Such additives may include other surfactants that can be used in admixture with the film forming surfactants and most of which are recited in the prior art discussed in the introduction of this specification. For instance, one may cite free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyakylated; mono-, di- and triglycerides of saturated or unsaturated fatty acids; glycerides of soya-oil and sucrose. The amount of the non-film forming tensides or surfactants can be up to 50% by weight of the total amount of surfactants in the composition but is preferably between zero and 30%.

The total amount of surfactants relative to the aqueous carrier liquid is best in the range of 0.01 to 25% by weight but quantities in the range 0.5–5% are advantageous because one always tries to keep the amount of active substances in an injectable solution as low as possible, this being to minimize the introduction of foreign materials into living beings even when they are harmless and physiologically compatible.

Further optional additives to the surfactants include:

a) substances which are known to provide a negative charge on liposomes, for example, phosphatidic acid, phosphatidyl-glycerol or dicetyl phosphate;

b) substances known to provide a positive charge, for example, stearyl amine, or stearyl amine acetate;

c) substances known to affect the physical properties of the lipid films In a more desirable way: for example, capro-lactam and/or sterols such as cholesterol, ergosterol, phytosterol, sitosterol, sitosterol pyroglutamate, 7-dehydro-cholesterol or lanosterol, may affect lipid films rigidity;

d) substances known to have antioxidant properties to improve the chemical stability of the components in the suspensions, such as tocopherol, propyl gallate, ascorbyl palmitate, or butylated hydroxy toluene.

The aqueous carrier in this invention is mostly water with possibly small quantities of physiologically compatible liquids such as isopropanol, glycerol, hexanol and the like (see for instance EP-A- 52.575). In general the amount of the organic hydrosoluble liquids will not exceed 5–10% by weight.

The present composition may also contain dissolved or suspended therein hydrophilic compounds and polymers defined generally under the name of viscosity enhancers or stabilizers. Although the presence of such compounds is not compulsory for ensuring stability to the air or gas bubbles with time in the present dispersions, they are advantageous to give some kind of "body" to the solutions. When desired, the upper concentrations of such additives when totally innocuous can be very high, for instance up to 80–90% by weight of solution with Iopamidol and other iodinated X-ray contrast agents. However with other viscosity enhancers like for instance sugars, e.g. lactose, sucrose, maltose, galactose, glucose, etc. or hydrophilic polymers like starch, dextran, polyvinyl alcohol, polyvinyl-pyrrolidone, dextrin, xanthan or partly hydrolyzed cellulose oligomers, as well as proteins and polypeptides, the concentrations are best between about 1 and 40% by weight, a range of about 5–20% being preferred.

Like in the prior art, the injectable compositions of this invention can also contain physiologically acceptable electrolytes; an example is an isotonic solution of salt.

The present invention naturally also includes dry storable pulverulent blends which can generate the present microbubble containing dispersions upon simple admixing with water or an aqueous carrier phase. Preferably such dry blends or formulations will contain all solid ingredients necessary to provide the desired microbubbles suspensions upon the simple addition of water, i.e. principally the surfactants in lamellar form containing trapped or adsorbed therein the air or gas required for microbubble formation, and accessorily the other non-film forming surfactants, the viscosity enhancers and stabilizers and possibly other optional additives. As said before, the air or gas entrapment by the laminated surfactants occurs by simply exposing said surfactants to the air (or gas) at room or super-atmospheric pressure for a time sufficient to cause said air or gas to become entrapped within the surfactant. This period of time can be very short, e.g. in the order of a few seconds to a few minutes although over-exposure, i.e. storage under air or under a gaseous atmosphere is in no way harmful. What is important is that air can well contact as much as possible of the available surface of the laminated surfactant, i.e. the dry material should preferably be in a "fluffy" light flowing condition. This is precisely this condition which results from the freeze-drying of an aqueous solution of liposomes and hydrophilic agent as disclosed in U.S. Pat. No. 4,229,360.

In general, the weight ratio of surfactants to hydrophilic viscosity enhancer in the dry formulations will be in the order of 0.1:10 to 10:1, the further optional ingredients, if any, being present in a ratio not exceeding 50% relative to the total of surfactants plus viscosity enhancers.

The dry blend formulations of this invention can be prepared by very simple methods. As seen before, one preferred method is to first prepare an aqueous solution in which the film forming lipids are laminarized, for instance by sonication, or using any conventional technique commonly used in the liposome field, this solution also containing the other desired additives, i.e. viscosity enhancers, non-film forming surfactants, electrolyte, etc., and thereafter freeze drying to a free flowable powder which is then stored in the presence of air or an entrappable gas.

The dry blend can be kept for any period of time in the dry state and sold as such. For putting it into use, i.e. for preparing a gas or air microbubble suspension for ultrasonic imaging, one simply dissolves a known weight of the dry pulverulent formulation in a sterile aqueous phase, e.g. water or a physiologically acceptable medium. The amount of powder will depend on the desired concentration of bubbles in the injectable product, a count of about $10^8$–$10^9$ bubbles/ml being generally that from making a 5–20% by weight solution of the powder in water. But naturally this figure is only indicative, the amount of bubbles being essentially dependent on the amount of air or gas trapped during manufacture of the dry powder. The manufacturing steps being under control, the dissolution of the dry formulations will provide microbubble suspensions with well reproducible counts.

The resulting microbubble suspensions (bubble in the 0.5–10 $\mu$m range) are extraordinarily stable with time, the count originally measured at start staying unchanged or only little changed for weeks and even months; the only observable change is a kind of segregation, the larger bubbles (around 10 $\mu$m) tending to rise faster than the small ones.

It has also been found that the microbubbles suspensions of this invention can be diluted with very little loss in the number of microbubbles to be expected from dilution, i.e. even in the case of high dilution ratios, e.g. $1/10^2$ to $1/10^4$, the microbubble count reduction accurately matches with the dilution ratio. This indicates that the stability of the bubbles depends on the surfactant in lamellar form rather than on the presence of stabilizers or viscosity enhancers like in the prior art. This property is advantageous in regard to imaging test reproducibility as the bubbles are not affected by dilution with blood upon injection into a patient.

Another advantage of the bubbles of this invention versus the microcapsules of the prior art surrounded by a rigid but breakable membrane which may irreversibly fracture under stress is that when the present suspensions are subject to sudden pressure changes, the present bubbles will momentarily contract elastically and then resume their original shape when the pressure is released. This is important in clinical practice when the microbubbles are pumped through the heart and therefore are exposed to alternating pressure pulses.

The reasons why the microbubbles in this invention are so stable are not clearly understood. Since to prevent bubble escape the buoyancy forces should equilibrate with the retaining forces due to friction, i.e. to viscosity, it is theorized that the bubbles are probably surrounded by the laminated surfactant. Whether this laminar surfactant is in the form of a continuous or discontinuous membrane, or even as closed spheres attached to the microbubbles, is for the moment unknown but under investigation. However the lack of a detailed knowledge of the phenomena presently involved does not preclude full industrial operability of the present invention.

The bubble suspensions of the present invention are also useful in other medical/diagnostic applications where it is desirable to target the stabilized microbubbles to specific sites in the body following their injection, for instance to thrombi present in blood vessels, to atherosclerotic lesions (plaques) in arteries, to tumor cells, as well as for the diagnosis of altered surfaces of body cavities, e.g. ulceration sites in the stomach or tumors of the bladder. For this, one can bind monoclonal antibodies tailored by genetic engineering, antibody fragments or polypeptides designed to mimic antibodies, bioadhesive polymers, lectins and other site-recognizing molecules to the surfactant layer stabilizing the microbubbles. Thus monoclonal antibodies can be bound to phospholipid bilayers by the method described by L. D. Leserman, P. Machy and J. Barbet ("Liposome Technology vol. III" p. 29 ed. by G. Gregoriadis, CRC Press 1984). In another approach a palmitoyl antibody is first synthesized and then incorporated in phospholipid bilayers following L. Huang, A. Huang and S. J. Kennel ("Liposome Technology vol. III" p. 51 ed. by G. Gregoriadis, CRC Press 1984). Alternatively, some of the phospholipids used in the present invention can be carefully selected in order to obtain preferential uptake in organs or tissues or increased half-life in blood. Thus GM1 gangliosides—or phosphatidylinositol-containing liposomes, preferably in addition to cholesterol, will lead to increased half-lifes in blood after intravenous administration in analogy with A. Gabizon, D. Papahadjopoulos, Proc. Natl Acad. Sci USA 85 (1988) 6949.

The gases in the microbubbles of the present invention can include, in addition to current innocuous physiologically acceptable gases like $CO_2$, nitrogen, $N_2O$, methane, butane, FREON and mixtures thereof, radioactive gases such as $^{133}$Xe or $^{81}$Kr are of particular interest in nuclear medicine for blood circulation measurements, for lung scintigraphy etc.

The following Examples illustrate the invention on a practical stand point.

Echogenic measurements

Echogenicity measurements were performed in a pulse—echo system made of a plexiglas specimen bolder (diameter 30 mm) and a transducer holder immersed in a constant temperature water bath, a pulser-receiver (Accutron M3010S) with for the receiving part an external pre-amplifier with a fixed gain of 40 dB and an internal amplifier with adjustable gain from −40 to ×40 dB. A 10 MHz low-pass filter was inserted in the receiving part to improve the signal to noise ratio. The A/D board in the IBM PC was a Sonotek STR 832. Measurements were carried out at 2.25, 3.5, 5 and 7.5 MHz.

EXAMPLE 1

A liposome solution (50 mg lipids per ml) was prepared in distilled water by the REV method (see F. Szoka Jr. and D. Papahadjopoulos, Proc. Natl. Acad. Sci. USA 75 (1978) 4194) using hydrogenated soya lecithin (NC 95 H, Nattermann Chemie, Köln, W. Germany) and dicetylphosphate in a molar ratio ⁹⁄₁. This liposome preparation was extruded at 65° C. (to calibrate the vesicle size) through a 1 μm polycarbonate filter (Nucleopore). Two ml of this solution were admixed with 5 ml of a 75% iopamidol solution in water and 0.4 ml of air and the mixture was forced back and forth through a two syringe system as disclosed in DE-A-3529195, while maintaining continuously a slight over-pressure. This resulted in the formation of a suspension of microbubbles of air in the liquid ($10^5$–$10^6$ bubbles per ml, bubble size 1–20 μm as estimated by light microscopy) which was stable for several hours at room temperature. This suspension gave a strong echo signal when tested by ultrasonic echography at 7.5, 5, 3.5 and 2.25 MHz.

EXAMPLE 2

A distilled water solution (100 ml) containing by weight 2% of hydrogenated soya lecithin and dicetylphosphate in a ⁹⁄₁ molar ratio was sonicated for 15 min at 60–65° C. with a Branson probe sonifier (Type 250).

After cooling, the solution was centrifuged for 15 min at 10,000 g and the supernatant was recovered and lactose added to make a 7.5% b. w. solution. The solution was placed in a tight container in which a pressure of 4 bar of nitrogen was established for a few minutes while shaking the container. Afterwards, the pressure was released suddenly whereby a highly concentrated bubble suspension was obtained ($10^{10}$–$10^{11}$ bubbles/ml). The size distribution of the bubbles was however wider than in Example 1, i.e. from about 1 to 50 μm. The suspension was very stable but after a few days a segregation occurred in the standing phase, the larger bubbles tending to concentrate in the upper layers of the suspension.

EXAMPLE 3

Twenty g of glass beads (diameter about 1 mm) were immersed into a solution of 100 mg of dipalmitoylphos-phatidylcholine (Fluka A. G. Buchs) in 10 ml of chloroform. The beads were rotated under reduced pressure in a rotating evaporator until all $CHCl_3$ had escaped. Then the beads were further rotated under atmospheric pressure for a few minutes and 10 ml of distilled water were added. The beads were removed and a suspension of air microbubbles was obtained which was shown to contain about $10^6$ bubbles/ml after examination under the microscope. The average size of the bubbles was about 3–5 μm. The suspension was stable for several days at least.

EXAMPLE 4

A hydrogenated soya lecithin/dicetylphosphate suspension in water was laminarized using the REV technique as described in Example 1. Two ml of the liposome preparation were added to 8 ml of 15% maltose solution in distilled water. The resulting solution was frozen at −30° C., then lyophilized under 0.1 Torr. Complete sublimation of the ice was obtained in a few hours. Thereafter, air pressure was restored in the evacuated container so that the lyophilized powder became saturated with air in a few minutes.

The dry powder was then dissolved in 10 ml of sterile water under gentle mixing, whereby a microbubble suspension ($10^8$–$10^9$ microbubbles per ml, dynamic viscosity (<20 mPa·s) was obtained. This suspension containing mostly bubbles in the 1–5 μm range was stable for a very long period, as numerous bubbles could still be detected after 2 months standing. This microbubble suspension gave a strong response in ultrasonic echography. If in this example the solution is frozen by spraying in air at −30 to −70° C. to obtain a frozen snow instead of a monolithic block and the snow is then evaporated under vacuum, excellent results are obtained.

EXAMPLE 5

Two ml samples of the liposome solution obtained as described in Example 4 were mixed with 10 ml of an 5% aqueous solution of gelatin (sample 5A), human albumin (sample 5B) dextran (sample 5C) and iopamidol (sample 5D). All samples were lyophilized. After lyophilization and introduction of air, the various samples were gently mixed with 20 ml of sterile water. In all cases, the bubble concentration was above $10^8$ bubbles per ml and almost all bubbles were below 10 μm. The procedure of the foregoing Example was repeated with 9 ml of the liposome preparation (450 mg of lipids) and only one ml of a 5% human albumin solution. After lyophilization, exposure to air and addition of sterile water (20 ml), the resulting solution contained 2 ×$10^8$ bubbles per ml, most of them below 10 μm.

EXAMPLE 6

Lactose (500 mg), finely milled to a particle size of 1–3 μm, was moistened with a chloroform (5 ml) solution of 100 mg of dimyristoylphosphatidylcholine/cholesterol/dipalmitoylphosphatidic acid (from Fluka) in a molar ratio of 4:1:1 and thereafter evaporated under vacuum in a rotating evaporator. The resulting free flowing white powder was rotated a few minutes under nitrogen at normal pressure and thereafter dissolved in 20 ml of sterile water. A microbubble suspension was obtained with about $10^5$–$10^6$ microbubbles per ml in the 1–10 μm size range as ascertained by observation under the microscope. In this Example, the weight ratio of coated surfactant to water-soluble carrier was 1:5. Excellent results ($10^7$–$10^8$ microbubbles/ml) are also obtained when reducing this ratio to lower values, i.e. down to 1:20, which will actually increase the surfactant efficiency for the intake of air, that is, this will decrease the weight of surfactant necessary for producing the same bubble count.

EXAMPLE 7

An aqueous solution containing 2% of hydrogenated soya lecithin and 0.4% of Pluronic® F68 (a non ionic polyoxyethylene-polyoxypropylene copolymer surfactant) was sonicated as described in Example 2. After cooling and centrifugation, 5 ml of this solution were added to 5 ml of a 15% maltose solution in water. The resulting solution was frozen at −30° C. and evaporated under 0.1 Torr. Then air pressure was restored in the vessel containing the dry powder. This was left to stand in air for a few seconds, after which it was used to make a 10% by weight aqueous solution which showed under the microscope to be a suspension of very tiny bubbles (below 10 μm); the bubble concentration was in the range of $10^7$ bubbles per ml. This preparation gave a very strong response in ultrasonic echography at 2.25, 3.5, 5 and 7.5 MHz.

EXAMPLE 8

Two-dimensional echocardiography was performed in an experimental dog following peripheral vein injection of 0.1–2 ml of the preparation obtained in Example 4. Opacification of the left heart with clear outlining of the endocardium was observed, thereby confirming that the microbubbles (or at least a significant part of them) were able to cross the pulmonary capillary circulation.

EXAMPLE 9

A phospholipid/maltose lyophilized powder was prepared as described in Example 4. However, at the end of the lyophilization step, a $^{133}$Xe containing gas mixture was introduced in the evacuated container instead of air. A few minutes later, sterile water was introduced and after gentle mixing a microbubble suspension containing $^{133}$Xe in the gas phase was produced. This microbubble suspension was injected into living bodies to undertake investigations requiring use of $^{133}$Xe as tracer. Excellent results were obtained.

EXAMPLE 10 (COMPARATIVE)

In U.S. Pat. No. 4,900,540, Ryan et al disclose gas filled liposomes for ultrasonic investigations. According to the citation, liposomes are formed by conventional means but with the addition of a gas or gas precursor in the aqueous composition forming the liposome core (col. 2, lines 15–27).

Using a gas precursor (bicarbonate) is detailed in Examples 1 and 2 of the reference. Using an aqueous carrier with an added gas for encapsulating the gas in the liposomes (not examplified by Ryan et al) will require that the gas be in the form of very small bubbles, i.e. of size similar or smaller than the size of the liposome vesicles.

Aqueous media in which air can be entrapped in the form of very small bubbles (2.5–5 μm) are disclosed in H. W. Keller et al, J. Ultrasound Med. 5 (1986), 413–498.

A quantity of 126 mg of egg lecithin and 27 mg of cholesterol were dissolved in 9 ml of chloroform in a 200 ml round bottom flask. The solution of lipids was evaporated to dryness on a Rotavapor whereby a film of the lipids was formed on the walls of the flask. A 10 ml of a 50% by weight aqueous dextrose solution was sonicated for 5 min according to M. W. Keller et al (ibid) to generate air microbubbles therein and the sonicated solution was added to the flask containing the film of lipid, whereby hand agitation of the vessel resulted into hydration of the phospholipids and formation of multilamellar liposomes within the bubbles containing carrier liquid.

After standing for a while, the resulting liposome suspension was subjected to centrifugation under 5000 g for 15 min to remove from the carrier the air not entrapped in the vesicles. It was also expected that during centrifugation, the air filled liposomes would segregate to the surface by buoyancy.

After centrifugation the tubes were examined and showed a bottom residue consisting of agglomerated dextrose filled liposomes and a clear supernatant liquid with substantially no bubble left. The quantity of air filled liposomes having risen by buoyancy was negligibly small and could not be ascertained.

EXAMPLE 11 (COMPARATIVE)

An injectable contrast composition was prepared according to Ryan (U.S. Pat. No. 4,900,540, col. 3, Example 1). Egg lecithin (126 mg) and cholesterol (27 mg) were dissolved in 9 ml of diethylether. To the solution were added 3 ml of 0.2 molar aqueous bicarbonate and the resulting two phase systems was sonicated until becoming homogeneous. The mixture was evaporated in a Rotavapor apparatus and 3 ml of 0.2 molar aqueous bicarbonate were added.

A 1 ml portion of the liposome suspension was injected into the jugular vein of an experimental rabbit, the animal being under condition for heart ultrasonic imaging-using an Acuson 128-XP5 ultrasonic imager (7.5 transducer probe for imaging the heart). The probe provided a cross-sectional image of the right and left ventricles (mid-papillary muscle). After injection, a light and transient (a few seconds) increase in the outline of the right ventricle was observed. The effect was however much inferior to the effect observed using the preparation of Example 4. No improvement of the imaging of the left ventricle was noted which probably indicates that the $CO_2$ loaded liposomes did not pass the pulmonary capillaries barrier.

We claim:

1. A dry pulverulent formulation which, upon dissolution in water, will form an aqueous suspension of stabilized air or gas microbubbles useful in ultrasonic imaging, the formulation comprising at least one film forming surfactant and at least one hydrophilic stabilizer in the presence of air or other entrappable gas, the film forming surfactant being a saturated phospholipid in lamellar or laminar form.

2. The dry formulation of claim 1, wherein the phospholipid is phosphatidic acid.

3. The dry formulation of claim 1, wherein the phospholipid is phosphatidylcholine.

4. The dry formulation of claim 1, wherein the phospholipid is phosphatidylethanolamine.

5. The dry formulation of claim 1, wherein the phospholipid is phosphatidylserine.

6. The dry formulation of claim 1, wherein the phospholipid is phosphatidylglycerol.

7. The dry formulation of claim 1, wherein the phospholipid is phosphatidylinositol.

8. The dry formulation of claim 1, wherein the phospholipid is cardiolipin.

9. The dry formulation of claim 1, wherein the phospholipid is sphyngomyelin.

10. The dry formulation of claim 1, wherein the formulation further contains dicetylphosphate.

11. The dry formulation of claim 1, wherein the formulation further contains cholesterol.

12. The dry formulation of claim 1, wherein the formulation further contains ergosterol.

13. The dry formulation of claim 1, wherein the formulation further contains phytosterol.

14. The dry formulation of claim 1, wherein the formulation further contains sitosterol.

15. The dry formulation of claim 1, wherein the formulation further contains lanosterol.

16. The dry formulation of claim 1, wherein the formulation further contains tocopterol.

17. The dry formulation of claim 1, wherein the formulation further contains propyl gallate.

18. The dry formulation of claim 1, wherein the formulation further contains ascorbyl palmitate.

19. The dry formulation of claim 1, wherein the formulation further contains butylated hydroxy-toluene.

20. The dry formulation of claim 1, further containing dissolved viscosity enhancers or stabilizers in a weight ratio to the surfactants comprised between about 1:5 to 100:1.

21. The dry formulation of claim 20, wherein the viscosity enhancers are linear and cross-linked polysaccharides.

22. The dry formulation of claim 20, wherein the viscosity enhancers are linear and cross-linked oligo-saccharides.

23. The dry formulation of claim 20, wherein the viscosity enhancers are sugars or hydrophilic polymers.

24. The dry formulation of claim 1, wherein the formulation comprises up to 50% by weight of non-laminar surfactants.

25. The dry formulation of claim 24, wherein the non-laminar surfactant is a fatty acid.

26. The dry formulation of claim 24, wherein the non-laminar surfactant is an ester or ether of fatty acids and alcohols.

27. The dry formulation of claim 24, wherein the non-laminar surfactant is a polyalkylene glycols.

28. The dry formulation of claim 24, wherein the non-laminar surfactant is a carbohydrate.

29. The dry formulation of claim 24, wherein the non-laminar surfactant is a polyalkylenated glycerol.

30. The dry formulation of claim 1, wherein the phospholipids in laminar form are in the form of fine layers deposited on the surface of soluble or insoluble solid particulate material.

31. The dry formulation of claim 30, wherein the insoluble solid particulate material is glass or polymer beads.

32. The dry formulation of claim 30, wherein the soluble particles are made of hydrosoluble carbohydrates or polysaccharides.

33. The dry formulation of claim 30, wherein the soluble particle are made of synthetic polymers or Iopamidol.

34. The dry formulation of claim 30, wherein the soluble particles are made of albumin or gelatin.

35. The dry formulation of claim 1, in the form of freeze-dried liposomes.

36. The dry formulation of claim 1, wherein the size of a majority of the microbubbles is below 50 $\mu$m.

37. The dry formulation of claim 1, wherein the suspension contains about $10^8$ to $10^9$ bubbles of 0.5 to 10 $\mu$m size/ml.

38. The dry formulation of claim 1, wherein the entrappable gas is a freon, nitrogen, carbon dioxide, argon, methane or mixtures thereof.

39. The dry formulation of claim 1, wherein the entrappable gas is a freon.

40. The dry formulation of claim 1, wherein the entrappable gas is $^{81}$kripton or $^{133}$xeonon.

41. The dry formulation of claim 38, wherein the entrappable gas is a halogenated hydrocarbon gas.

42. The dry formulation of claim 1, wherein the entrappable gas is nitrogen.

43. The dry formulation of claim 1, wherein the entrappable gas is carbon dioxide.

44. The dry formulation of claim 1, wherein the entrappable gas is argon.

45. The dry formulation of claim 1, wherein the entrappable gas is methane.

46. The dry formulation of claim 1, wherein the hydrophilic stabilizer is a hydrosoluble protein.

47. The dry formulation of claim 1, wherein the hydrophilic stabilizer is a polypeptide.

48. The dry formulation of claim 1, wherein the hydrophilic stabilizer is a sugar.

49. The dry formulation of claim 1, wherein the hydrophilic stabilizer is a poly- or oligo-saccharide.

50. The dry formulation of claim 1, wherein the hydrophilic stabilizer is a hydrophilic polymer.

* * * * *

UNITED STATES PATENT AND TRADEMARK OFFICE
CERTIFICATE OF CORRECTION

PATENT NO. : 6,110,443
DATED : August 29, 2000
INVENTOR(S) : M. Schneider et al.

Page 1 of 1

It is certified that error appears in the above-identified patent and that said Letters Patent is hereby corrected as shown below:

Title page,
Item [62], line 4, after "08/128,540," insert -- Sept. 29, 1993, now --.
Line 4, delete "filed as application".
Line 5, delete "No. PCT/EP91/00620, Apr. 2, 1991,".
Line 5, after "5,380,519," insert -- which is --.
Line 5, delete "and".
Line 6, after "1991," insert -- which is the national stage of PCT/EP91/00620, now --.

Column 1,
Line 10, delete "371 of PCT/EP91/00620 filed Apr. 2, 1991 and is a".
Line 11, after "1991," insert -- which is a 371 of PCT/EP91/00620, filed Apr. 2, 1991 --.

Signed and Sealed this

First Day of January, 2002

Attest:

Attesting Officer

JAMES E. ROGAN
Director of the United States Patent and Trademark Office